United States Patent [19]
Gray

[11] Patent Number: 5,885,547
[45] Date of Patent: Mar. 23, 1999

[54] PARTICULATE MATERIAL

[75] Inventor: Bruce Nathaniel Gray, Claremont, Australia

[73] Assignee: Paragon Medical Ltd., West Perth Western, Australia

[21] Appl. No.: 676,381

[22] PCT Filed: Jan. 20, 1995

[86] PCT No.: PCT/AU95/00027

§ 371 Date: Sep. 23, 1996

§ 102(e) Date: Sep. 23, 1996

[87] PCT Pub. No.: WO95/19841

PCT Pub. Date: Jul. 27, 1995

[30] Foreign Application Priority Data

Jan. 21, 1994 [AU] Australia .............................. 54724/24

[51] Int. Cl.⁶ .................................................. A61K 51/00
[52] U.S. Cl. ...................... 424/1.37; 424/1.11; 424/1.29; 424/1.33; 424/1.65
[58] Field of Search ................................ 424/1.11, 1.29, 424/1.33, 1.37, 1.65, 9.1, 9.321, 9.323, 9.36, 9.4, 9.42, 9.5, 400, 450, 455, 458

[56] References Cited

U.S. PATENT DOCUMENTS

| | | | |
|---|---|---|---|
| 3,365,315 | 1/1968 | Beck et al. ................................. | 106/40 |
| 4,039,480 | 8/1977 | Watson et al. ........................... | 252/455 |
| 4,290,847 | 9/1981 | Johnson et al. .............................. | 176/1 |
| 4,303,433 | 12/1981 | Torobin ..................................... | 65/21.4 |
| 4,340,642 | 7/1982 | Netting et al. ........................... | 428/402 |
| 4,349,456 | 9/1982 | Sowman ................................... | 252/317 |
| 4,411,847 | 10/1983 | Netting et al. .............................. | 264/7 |
| 4,547,468 | 10/1985 | Jones et al. ................................ | 501/33 |
| 4,772,511 | 9/1988 | Wood et al. ............................. | 428/325 |
| 4,789,501 | 12/1988 | Day et al. ................................. | 252/645 |
| 4,874,726 | 10/1989 | Kleeb et al. ............................. | 501/124 |
| 4,889,707 | 12/1989 | Day et al. ................................. | 424/1.11 |
| 5,011,677 | 4/1991 | Day et al. ................................. | 424/1.11 |
| 5,011,797 | 4/1991 | Day et al. ................................. | 501/33 |
| 5,039,326 | 8/1991 | Day et al. ................................. | 424/1.11 |
| 5,302,369 | 4/1994 | Day et al. ................................. | 424/1.29 |

FOREIGN PATENT DOCUMENTS

| | | |
|---|---|---|
| 0182131 | 5/1986 | European Pat. Off. . |
| 0369638 | 5/1990 | European Pat. Off. . |
| 2073589 | 10/1981 | United Kingdom . |
| WO 8602093 | 4/1986 | WIPO . |
| WO 9314788 | 8/1993 | WIPO . |

*Primary Examiner*—JoséG. Dees
*Assistant Examiner*—Dameron Jones
*Attorney, Agent, or Firm*—Baker & Botts, L.L.P.

[57] ABSTRACT

A particulate material which comprises hollow or cup-shaped ceramic microspheres having a diameter in the range of from 5 to 200 microns. The material may comprise a beta- or gamma-emitting radionuclide and be used in selective internal radiation therapy (SIRT) of various forms of cancer and tumours.

10 Claims, No Drawings

PARTICULATE MATERIAL

This application is a 371 of PCT/AU95/00027 filed Jan. 20, 1995.

FIELD OF THE INVENTION

This invention relates to a particulate material which comprises small hollow or cup-shaped ceramic particles (hereinafter referred to as "microspheres"), to a process for the production thereof, and to methods for the use of this particulate material.

In one particular aspect, this invention relates to hollow or cup-shaped ceramic microspheres which consist of or comprise a radioactive material, and to the use of these radioactive microspheres in the treatment of cancer in humans and other mammals. In this aspect, the radioactive microspheres are designed to be administered into the arterial blood supply of the organ to be treated, whereby they become entrapped in the small blood vessels of the target organ and irradiate it. An alternate form of administration is to inject the radioactive microspheres directly into the tumour to be treated.

The particulate material of the present invention therefore has utility in the treatment of various forms of cancer and tumours, but particularly in the treatment of primary and secondary cancer of the liver and the brain. It is, however, to be understood that this invention is not limited to microspheres of radioactive material, and extends to microspheres of other ceramic materials which are suitable for use in the process described herein.

BACKGROUND OF THE INVENTION

Many previous attempts have been made to locally administer radioactive materials to patients with cancer as a form of therapy. In some of these, the radioactive materials have been incorporated into small particles, seeds, wires and similar related configurations that can be directly implanted into the cancer. In other approaches, the radioactive materials have been formulated into microspheres of regular size for injection into the arterial blood supply of the target organ. When radioactive particles or microspheres are administered into the blood supply of the target organ, the technique has become known as Selective Internal Radiation Therapy (SIRT). Generally, the main form of application of SIRT has been its use to treat cancers in the liver.

There are many potential advantages of SIRT over conventional, external beam radiotherapy. Firstly, the radiation is delivered preferentially to the cancer within the target organ. Secondly, the radiation is slowly and continually delivered as the radionuclide decays. Thirdly, by manipulating the arterial blood supply with vasoactive substances (such as Angiotensin-2), it is possible to enhance the percentage of radioactive microspheres that go to the cancerous part of the organ, as opposed to the healthy normal tissues. This has the effect of preferentially increasing the radiation dose to the cancer while maintaining the radiation dose to the normal tissues at a lower level (Burton, M. A. et al.; Effect of Angiotensin-2 on blood flow in the transplanted sheep squamous cell carcinoma. *Europ. J. Cancer Clin. Oncol.* 1988, 24(8):1373–1376).

When microspheres or other small particles are administered into the arterial blood supply of a target organ, it is desirable to have them of a size, shape and density that results in the optimal homogeneous distribution within the target organ. If the microspheres or small particles do not distribute evenly, and as a function of the absolute arterial blood flow, then they may accumulate in excessive numbers in some areas and cause focal areas of excessive radiation. It has been shown that microspheres of approximately 25–50 micron in diameter have the best distribution characteristics when administered into the arterial circulation of the liver (Meade, V. et al.; Distribution of different sized microspheres in experimental hepatic tumours. *Europ. J. Cancer & Clin. Oncol.* 1987, 23:23–41).

If the microspheres or small particles do not contain sufficient ionising radiation, then an excessive number will be required to deliver the required radiation dose to the target organ. It has been shown that if large numbers of microspheres are administered into the arterial supply of the liver, then they accumulate in and block the small arteries leading to the tumour, rather than distribute evenly in the capillaries and precapillary arterioles of the tumour. Therefore, it is desirable to use the minimum number of microspheres that will provide an even distribution in the vascular network of the tumour circulation.

Similarly if the microspheres or small particles are too dense or heavy, then they will not distribute evenly in the target organ and will accumulate in excessive concentrations in parts of the liver that do not contain the cancer. It has been shown that solid heavy microspheres distribute poorly within the parenchyma of the liver when injected into the arterial supply of the liver. This, in turn, decreases the effective radiation reaching the cancer in the target organ, which decreases the ability of the radioactive microspheres to kill the tumour cells. In contrast, lighter microspheres with a specific gravity of the order of 2.0 distribute well within the liver (Burton, M. A. et al.; Selective International Radiation Therapy; Distribution of radiation in the liver. *Europ. J. Cancer Clin. Oncol.* 1989, 25:1487–1491).

For radioactive microspheres to be used successfully for the treatment of cancer, the radiation emitted from the microspheres should be of high energy and short range. This ensures that the energy emitted from the microspheres will be deposited into the tissues immediately around the microspheres and not into tissues which are not the target of the radiation treatment. There are many radionuclides that can be incorporated into microspheres that can be used for SIRT. Of particular suitability for use in this form of treatment are the unstable isotopes of yttrium (Y-90) and phosphorous (P-32), although other isotopes such as iodine can also be used. Yttrium-90 is the unstable isotope of yttrium-89 which can be manufactured by placing the stable yttrium-89 in a neutron beam. The yttrium-90 that is generated decays with a half life of 64 hours, while emitting a high energy pure beta radiation.

If the microspheres contain other radioactive substances that are not required for the radiation treatment of the target tissue, then unwanted and deleterious radiation effects may occur. It is therefore desirable to have microspheres of such a composition that they only contain the single desired radionuclide. In this treatment mode, it is desirable to have microspheres that emit high energy but short penetration beta-radiation which will confine the radiation effects to the immediate vicinity of the microspheres. For this purpose, yttrium-90 is the preferred radionuclide, although other radionuclides such as P-32 are also suitable.

Therefore, the ideal microspheres for use in this treatment mode will consist only of yttria, have a low density relative to pure yttria, be in the size range of from 20–80 micron, and be stable so that no material leaches from the microspheres when administered into the body of a human or other mammalian patient.

In the earliest clinical use of yttrium-90-containing microspheres, the yttrium was incorporated into a polymeric matrix that was formulated into microspheres. While these microspheres were of an appropriate density to ensure good distribution characteristics in the liver, there were several instances in which the yttrium-90 leached from the microspheres and caused inappropriate radiation of other tissues.

In one attempt to overcome the problem of leaching, a radioactive microsphere comprising a biologically compatible glass material containing a beta- or gamma-radiation emitting radioisotope such as yttrium-90 distributed throughout the glass, has been developed (International Patent Publication No. WO 86/03124). These microspheres are solid glass and contain the element yttrium-89 which can be activated to the radionuclide yttrium-90 by placing the microspheres in a neutron beam. These glass microspheres have several disadvantages including being of a higher specific gravity than is desirable, containing other elements such as alumina and silica which are activated to undesirable radionuclides when placed in a neutron beam, and requiring large numbers of microspheres in order to deliver the required amount of radiation to the target tissue.

There have been several reports of clinical studies on the use of solid glass radioactive microspheres. In one report, ten patients with primary hepatocellular carcinoma were treated, however no patient had a complete or partial response (Shepherd, F. et al., Cancer, Nov. 1, 1992, Vol. 70, No. 9, pp 2250–2254).

A further development in order to overcome the problem of leaching, was the production of light polymeric ion-exchange microspheres that did not leach their yttrium content when injected into the body. Using these microspheres, a high objective response rate for patients with secondary cancer in the liver was obtained when the microspheres were injected into the hepatic artery (Gray, B. N. et al. Regression of liver metastases following treatment with Yttrium-90 microspheres. Aust. N.Z. J. Surg. 1992, 62:105–110). One disadvantage of such polymeric ion exchange microspheres is that the yttrium-90 radionuclide must be added to the microsphere after neutron activation of the stable isotope of yttrium-89. This requires the use of specialised facilities and potentially is hazardous to the manufacturing personnel. Furthermore, the polymeric microspheres contain only a low percentage of yttrium.

Using the technique described by Gray et al., other clinical studies in patients with secondary liver cancer have demonstrated a very high response rate using low density yttrium-90 containing microspheres. In one study in patients with metastatic liver cancer, the majority of patients benefited from treatment with radioactive microspheres with appropriate physical characteristics, specially when combined with perfusion of cytotoxic drugs into the arterial circulation of the liver (Gray, B. N. et al., supra).

SUMMARY OF THE INVENTION

In one aspect, the present invention provides a particulate material comprising hollow or cup-shaped ceramic microspheres having a diameter in the range of from 5 to 200 microns.

In another aspect, this invention provides a process for the production of a particulate material as described above which comprises the steps of (a) forming aggregates of powdered ceramic base material with a suitable binder, (b) heating the aggregates to melt the base material and vaporise the binder to form hollow or cup-shaped microspheres, and (c) solidifying the molten hollow or cup-shaped microspheres.

Preferably, the process for the production of the particulate material comprises the steps of (i) grinding or otherwise reducing the ceramic base material to a fine powder, (ii) combining the base material with a suitable binder to form a slurry, (iii) spray drying the slurry in order to form aggregates of the base material combined with the binder, (iv) thermal spraying the spray dried aggregates so that the base material is melted and the binder vaporises resulting in distension of the molten base material so as to form hollow or cup-shaped microspheres, and (v) solidification of the molten hollow or cup-shaped microspheres, for example by collection in a cold medium such as water. The microspheres are then sorted into batches based on size and density to obtain microspheres having a diameter in the range of from 5 to 200 microns.

The microspheres may consist of or comprise any suitable ceramic base material or combination of base materials, including by way of example, yttria, alumina, zirconia or silica, or combinations thereof. Suitable combinations include, by way of example, the biologically compatible glass materials disclosed in International Patent Publication No. WO 86/03124, the disclosure of which is incorporated herein by reference. In addition to the oxides mentioned above, other compounds containing yttrium, aluminium, zirconium or silica which are suitable for forming the particulate material of this invention may also be used as the base material.

In a particularly preferred embodiment of this invention, the microspheres comprise yttria or another yttrium-containing compound or salt of yttrium as the base material component thereof. These preferred microspheres may be rendered radioactive by exposure to a neutron beam that activates the base material to the material radionuclide yttrium-90. In addition, these preferred microspheres do not leach the base material of which they are composed, and are biologically compatible.

The present invention further extends to a radioactive particulate material comprising hollow or cup-shaped ceramic microspheres, said microspheres comprising a beta- or gamma-radiation emitting radionuclide and having a diameter in the range of from 5 to 200 microns.

Preferably, the beta-radiation emitting radionuclide is yttrium-90.

The present invention also provides a method of radiation therapy of human or other mammalian patient, which comprises administration to the patient of a radioactive particulate material as described above.

In yet another aspect, this invention also extends to the use of a radioactive particulate material as described above in radiation therapy of a human or other mammalian patient.

DETAILED DESCRIPTION OF THE INVENTION

In order to overcome the problem of leaching of radionuclide from ceramic microspheres, while at the same time maintaining the microspheres with a low density, the present invention provides microspheres with improved characteristics arising from the fact that the microspheres are either hollow or cup-shaped. These microspheres can be formulated to be of such a size, shape and density that they have improved distribution characteristics when administered into the arterial supply of target organs to be treated. In addition, as they may be composed entirely of yttria, each microsphere can deliver a higher amount of ionising radiation than prior art microspheres. This, in turn, means that a lesser number can be administered to the target organ in order to deliver the same radiation dose. In another improvement, since the composition of the microspheres may be of pure yttria, unwanted ionising radiation emanating from unwanted radionuclides in the microspheres is thereby avoided. In another improvement, the microspheres can be neutron activated after manufacture, thereby improving the manufacture process.

In the following detailed description, reference is made in particular to the production and use of hollow or cup-shaped yttria microspheres in accordance with this invention. It is to be understood, however, that this description is equally applicable to the production of similar microspheres using other suitable ceramic base materials as described above.

In the production of hollow or cup-shaped ceramic microspheres in accordance with this invention, aggregates or agglomerates of powdered ceramic base material with a suitable binder material are formed. The purpose of the binder is to provide enough adhesive quality and strength to stabilise the aggregates, preferably in substantially spherical form. The maximum particle size of the aggregates is generally approximately 75 microns, and typically is in the range of 5 to 50 microns. The particulate size should be as uniform as possible to achieve best results in subsequent processing. Preferably, the aggregates are formed by agglomeration of fine powdered ceramic base material (for example, powder of approximately 0.1 up to several microns) using the spray drying technique in which the fine powder is mixed with a suitable binder and liquid to form a slurry. The slurry is then pumped to an atomiser where it is broken up into a large number of small droplets and dried using hot air to produce the resultant aggregates, generally in substantially spherical form.

The aggregates are then heated to melt the base material, preferably using the process of thermal or plasma spraying (for example, using a D.C. plasma jet) in which very high temperatures of approximately 17000° C. may be attained to ensure complete melting of the ceramic base material and vaporisation or volatilisation of the binder material. In plasma spraying the aggregates are introduced using a carrier gas such as argon into the plasma torch which uses a high temperature plasma such as argon, helium, hydrogen, or nitrogen, or mixtures thereof in the form of a plasma. The ceramic base material becomes molten and is then accelerated to a high velocity to be subsequently rapidly solidified, for example by collection in a body of water. During the plasma spraying, hollow or cup-shaped particles are formed due to the presence of large gas bubbles trapped within the molten material.

After solidification, microspheres comprises of or containing yttrium-containing compounds such as yttria, can then be irradiated in a neutron beam to result in the formation of the radioactive isotope yttrium-90 which is suitable for administration to patients.

During the production process, some microspheres do not form hollow spheres but take on a cup-shaped configuration. The cup-shaped particles are of similar size to the hollow microspheres. The presence of these cup-shaped particles does not significantly alter the characteristics of the batch of microspheres that are produced, and mixtures of both hollow and cup-shaped microspheres can be used for administration to patients. The invention therefore also includes the production of cup-shaped microspheres of a size distribution similar to that of hollow microspheres. In addition, whilst some microspheres may contain only one hollow pore or void, others may contain more than one such hollow pore or void. Once again, the presence of more than one pore in these hollow microspheres does not significantly alter the characteristics of the microspheres and accordingly the term "hollow microsphere" as used herein is to be understood as encompassing both microspheres with a single hollow pore or void, and microspheres with more than one hollow pore or void.

The thermal spraying technique results in microspheres with a variable size range. Microspheres of the desired size of from 5 to 200 micron can be sorted by a process of sieving, or using other well described techniques for sorting of small particles based on size. Similarly, the microspheres can be sorted into batches of similar density using conventional techniques for separating particles on the basis of density.

One example of a suitable binding material which may be used to bind the powdered base material during the spray drying process is polyvinyl alcohol. It will be appreciated that other binding materials can also be used to bind the base material for spray drying. The amount of binder material which is used may be varied as desired. Typically, however amounts of binder material of between 0.5 and 8 wt %, based on the dry weight of the powdered ceramic base material, may be used.

Preferably, yttria microspheres are produced by first grinding the yttria base material to a fine powder, for example up to several microns in diameter, and then spray drying the powder in the form of a slurry to form aggregates of the base material. The slurry contains a binding material which allows the formation of aggregates when fed through a spray drying apparatus. The spray dried aggregates can then be fed into a thermal jet (e.g. D.C. plasma jet) which results in the melting of the spray dried particles. The binding material used in the slurry during the spray drying process vaporises in the thermal jet during the process of melting of the yttria and distends the microspheres into the form of hollow or cup-shaped particles. The particles are then solidified, preferably by collection in a cold medium such as water.

In one embodiment of this invention, there is provided a method by which yttria can be thermally sprayed so as to form hollow or cup-shaped microspheres with the desired shape and density for use in the treatment of various forms of cancer and tumours, particularly in the liver and brain. These microspheres are composed of pure yttria, with a preferred size range of from 20 to 80 micron in diameter. The hollow or cup-shaped yttria microspheres are placed in a neutron beam to activate the yttria to the unstable isotope yttrium-90, and the radioactive microspheres can then be used in the treatment of cancers and/or tumours as described above.

The process that controls the formation of hollow or cup-shaped yttria microspheres is not limited to yttria and has been shown to also cause the formation of similar microspheres of other ceramic materials that can be melted and solidified by the process of thermal spraying, of which alumina, zirconia and silica are some examples.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Further features of the present invention are more fully described in the following Examples. It is to be understood, however, that this detailed description is included solely for the purposes of exemplifying the present invention, and should not be understood in any way as a restriction on the broad description of the invention as set out above.

EXAMPLE 1

In one representative experiment to produce microspheres of the present invention, 99.99% pure yttria was crushed in an attrition mill using zirconia particles for 11 hours to produce a fine yttria powder of approximately 1 micron diameter particles. The powder was dried and combined with polyvinyl alcohol as a binder to form a slurry. The slurry was fed through a spray drier which was set to produce dried particles of approximately 30 to 70 micron in diameter. The spray dried particles of yttria plus binder were initially sized to 36–53 micron by sieving and then fed into a DC plasma torch. In this representative production batch, a Plasmadyne SG-100 torch was used with an arc gas of argon/helium gas flow using argon as the carrier gas, under the following conditions:

| Arc Gas Flow Rate: | |
| --- | --- |
| Argon (L/min) | 40 |
| Helium (L/min) | 4 |
| Current (Amps) | 900 |
| Voltage (Volts) | 44.4 |
| Carrier Gas | Argon |

The above conditions have been determined to be the optimal torch conditions and yttria powder conditions to produce hollow yttria microspheres with a size range from 20 to 80 micron. Various other plasma torch conditions can be used with different current and voltage rates. The hollow microspheres so formed are then sized and sorted by density using a combination of sieving and density separation to produce the size range required for human or other mammalian use.

The microspheres are placed in a neutron beam to produce the beta-radiation emitting radionuclide yttrium-90.

EXAMPLE 2

The technique of Selective Internal Radiation Therapy (SIRT) has been described above. It involves either a laparotomy to expose the hepatic arterial circulation or the insertion of a catheter into the hepatic artery via the femoral, brachial or other suitable artery. This may be followed by the infusion of Angiotensin-2 into the hepatic artery to redirect arterial blood to flow into the metastatic tumour component of the liver and away from the normal parenchyma. This is followed by embolisation of yttrium-90 containing microspheres (produced in accordance with Example 1) into the arterial circulation so that they become lodged in the microcirculation of the tumour. Repeated injections of microspheres are made until the desired radiation level in the normal liver parenchyma is reached. By way of example, an amount of yttrium-90 activity that will result in an inferred radiation dose to the normal liver of approximately 80 Gy may be delivered. Because the radiation from SIRT is delivered as a series of discrete point sources, the dose of 80 Gy is an average dose with many normal liver parenchymal cells receiving much less than that dose.

The measurement of tumour response by objective parameters including reduction in tumour volume and serial estimations of serum carcino-embryonic antigen (CEA) levels, is an acceptable index of the ability of the treatment to alter the biological behaviour of the tumour.

EXAMPLE 3

Yttria ($Y_2O_3$) in the form of angular particles, approx. size range between 5 to 10 microns (Aldrich Chemical Co. Ltd.), used as starting material was subjected to wet attrition milling to reduce the particle size of the powder to <1 micron for subsequent spray drying. 1 kg of milling media (1 mm diameter yttria stabilised zirconia spheres obtained from Commercial Minerals Ltd.) was placed in a 1 l polyethylene container with up to 100 g of powder. Sufficient ethanol was added to fill the container to about 4 mm above the powder and milling media.

The powder was milled (approx. 11 hours) until the size of the majority of the particles was observed to be less than 1 micron (using a Scanning Electron Microscope (SEM)).

After milling, the milling media was separated from the powder using a 0.4 mm sieve. Distilled water was used to wash the milling media from any remaining powder. Vacuum filtration of the powder was then carried out using a Buchner funnel and Whatman filter paper No. 542. The powder was again washed with distilled water, and stored as wet slurry for spray drying.

Polyvinyl alcohol (PVA) was added as a binder at a concentration of 8 wt %, and the slurry spray dried at a slurry concentration of 38 wt % using a Niro Rotary Atomiser, Denmark. The size of the agglomerates produced by the spray drier could be controlled by the slurry feed rate and the rotational speed and diameter of the atomiser wheel. The inlet temperature (290°–300° C.) and the outlet temperature (100° C.) were monitored by thermocouples.

Prior to plasma spraying, the agglomerates were sieved using a 38 $\mu$m sieve to remove the fines while a 100 $\mu$m sieve was used to screen out the coarse particles.

The spray dried powder agglomerates were then plasma sprayed using a subsonic (atmospheric) D.C., plasma torch (Plasmadyne SG-100, 40 kW, 900 A). The plasma gases were Ar (44 l/min) and He (4 l/min). A Metco Powder Feed Unit Type 4MP Model 851 was used to feed the spray dried agglomerates into the plasma torch by using an argon carrier gas. In most cases the agglomerates were fed into the torch between 4–6 g/min. The plasma sprayed material was collected by directing it into distilled water contained in a stainless steel vessel. The surface of the water was 300 mm away from the torch head. After spraying, the water was decanted off and the material dried.

On examination of the surface morphology and internal structure of the plasma sprayed yttrium material using the scanning electron microscope (SEM), fully spheriodized $Y_2O_3$ particles having a generally smooth surface morphology were observed. Internally, pores were observed within most of the plasma sprayed material. While the distribution and amount of porosity differed, most $Y_2O_3$ particles contained a single spherical internal pore or void. In order to investigate the relationship between pore size and particle size, the "as prepared" plasma sprayed yttria material was sieved into different size ranges and the density of each size range measured using a pycnometer. The results are shown in the following Table, and show that the measured density decreased with an increase in particle size, indicating that the relative size of the pore within the particle increased with increasing particle size.

| Particle Size Range ($\mu$m) | Measured Density (kgm$^{-3}$) |
| --- | --- |
| <20 | 4.74 |
| 20–38 | 4.35 |
| 38–45 | 3.40 |
| 45–53 | 2.77 |
| 53–71 | 2.50 |

As described in Example 1 above, the plasma sprayed yttria material may then be placed in a neutron beam in order to produce beta-emitting radioactive particles.

I claim:

1. A process for the production of a particulate material comprising hollow or cup-shaped ceramic microspheres having a diameter in the range from 5 to 200 microns, which comprises the steps of
   (a) forming an aggregate of a powdered base material with a suitable binder,
   (b) thermal spraying of the aggregate to melt the base material and vaporize the binder to form the hollow or cup-shaped microspheres, and
   (c) solidifying the molten hollow or cup-shaped microspheres.

2. The process according to claim 1, wherein the binder is polyvinyl alcohol.

3. The process according to claim 1, wherein the base material comprises yttria, alumina, zirconia or silica, or other compounds containing yttrium, aluminum, zirconium or silicon, or combinations thereof.

4. The process according to claim 3, wherein the base material consists of yttria, alumina, zirconia or silica, or other compounds containing yttrium, aluminum, zirconium or silicon, or combinations thereof.

5. The process according to claim 3, wherein the base material comprises yttria or another yttrium-containing compound.

6. The process according to claim 5, wherein the base material consists of yttria or another yttrium-containing compound.

7. The process according to claim 1, wherein the microspheres have a diameter in a range from 20 to 80 microns.

8. The process according to claim 1, further comprising the step of
   (d) exposing the solidified hollow or cup-shaped microspheres to a neutron beam to activate the base material to a beta- or gamma-radiation emitting radionuclide.

9. The process according to claim 8, wherein the base material comprises yttria or another yttrium-containing compound and the radionuclide is yttrium-90.

10. The process according to claim 9, wherein the base material consists of yttria or another yttrium-containing compound and the radionuclide is yttrium-90.

* * * * *

UNITED STATES PATENT AND TRADEMARK OFFICE
CERTIFICATE OF CORRECTION

PATENT NO. : 5,885,547
DATED : March 23, 1999
INVENTOR(S) : Bruce Nathaniel Gray It is certified that error appears in the above-identified patent and that said Letters Patent is hereby corrected as shown below:

On the title page: Item [30]
Foreign Application Priority Data: "54724/24" should read -- 54724/94 --.

Item [73] Assignee:

"West Perth Western, Australia" should read --West Perth, Western Australia--;

Column 5, line 49, "comprises" should read --comprised--.

Signed and Sealed this

Twenty-eighth Day of November, 2000

Attest:

Attesting Officer

Q. TODD DICKINSON
Director of Patents and Trademarks